United States Patent
Barron

(10) Patent No.: US 11,285,044 B2
(45) Date of Patent: Mar. 29, 2022

(54) DONOR CORNEAL CUTTING BLADE

(71) Applicant: Mark B. Barron, Grand Blanc, MI (US)

(72) Inventor: Mark B. Barron, Grand Blanc, MI (US)

( * ) Notice: Subject to any disclaimer, the term of this patent is extended or adjusted under 35 U.S.C. 154(b) by 0 days.

(21) Appl. No.: 16/662,514

(22) Filed: Oct. 24, 2019

(65) Prior Publication Data

US 2021/0121328 A1    Apr. 29, 2021

(51) Int. Cl.
*A61F 9/013* (2006.01)

(52) U.S. Cl.
CPC .......... *A61F 9/0133* (2013.01); *A61F 9/0136* (2013.01)

(58) Field of Classification Search
CPC ...... A61F 9/013; A61F 9/0133; A61F 9/0136; A61F 9/007; A61F 2/14; A61F 2/142; A61F 2/148; A61F 2/145–1453; A61B 17/32053
USPC .......................................................... 606/166
See application file for complete search history.

(56) References Cited

U.S. PATENT DOCUMENTS

| | | | | |
|---|---|---|---|---|
| 4,907,587 A | * | 3/1990 | Fedorov | A61F 9/013 128/897 |
| 5,584,881 A | * | 12/1996 | Rowsey | A61F 9/013 623/5.15 |
| 5,649,944 A | * | 7/1997 | Collins | A61F 9/013 606/166 |
| 2005/0203554 A1 | * | 9/2005 | Dykes | A61B 90/39 606/166 |
| 2019/0380868 A1 | * | 12/2019 | Jacob | A61F 9/007 |

* cited by examiner

*Primary Examiner* — Darwin P Erezo
*Assistant Examiner* — Brigid K Byrd
(74) *Attorney, Agent, or Firm* — The Weintraub Group, P.L.C.

(57) ABSTRACT

A donor corneal tissue cutting blade provided with integrally formed asymmetrical markers for facilitation identification of the anterior and posterior sections or portions of the donor corneal tissue is disclosed. The blade is a cylindrical body having, in one embodiment, a U-shaped extension which cooperates with the body to define a keyway. Protrusions may be formed on the body and/or extension to provide further markers.

4 Claims, 3 Drawing Sheets

DONOR CORNEAL CUTTING BLADE

CROSS-REFERENCE TO RELATED APPLICATION

This application is a Completion Application of U.S. Provisional Patent Application, Ser. No. 62/773,493, filed on Nov. 30, 2018 for "Improved Donor Corneal Cutting Blade," the disclosure of which is hereby incorporated by reference, including the drawings.

BACKGROUND OF THE INVENTION

1. Field of the Invention

The present invention concerns ophthalmic corneal implants. More particularly, the present invention concerns corneal harvesting devices used in corneal transplantations. Even more particularly, the present invention concerns surgical cutting blades for harvesting donor tissue for corneal transplants.

2. Prior Art

In harvesting donor tissue for corneal graft procedures of the type referred to as Descemet's Membrane Endothelial Keratoplasty (DMEK) and Descemet's Stripping Endothelial Keratoplasty (DESK), thin layers of the anterior surface of the donor cornea is removed and then placed on the anterior surface of the patient cornea from which the endothelial layer has been removed. One of the difficulties with these procedures is knowing which side of the harvested tissue should be in the posterior section in the patient and which side should be the anterior section after placing the tissue into the anterior chamber of the patient's eye.

The typical method for identifying the proper orientation is to mark the posterior side of the donor tissue with Gentian Violet Ink using an asymmetrical symbol, such as the letter "S". As is known to the skilled artisan, this procedure for marking can be complicated. Further, the Gentian Violet Ink is a substance that, preferably, should not be injected into the anterior chamber of the eye. Thus, a method for cutting the donor corneal tissue in such a way as to properly identity the orientation, without the necessity for marking the donor tissue would provide a major advance in the art.

As detailed below, the present invention is directed to a cutting blade for facilitating orientation and identification of the anterior and posterior portions of the donor corneal tissue and which eliminates the need for Gentian Violet dye or ink.

SUMMARY OF THE INVENTION

In a first embodiment, the present invention provides a donor corneal cutting blade comprising a substantially cylindrical body and a tail integrally formed therewith which cooperates with the body to define a keyhole or keyway. The tail is in communication therewith.

The tail is a substantially U-shaped extension of the cylindrical body, having a height coextensive with that of the cylindrical body. The tail defines a marker identifying the anterior or posterior side of the corneal tissue. At least one protrusion on the body for enabling differentiation between the anterior and posterior portions of the donor tissue to enable proper placement. Optionally, at least one protrusion is provided on the tail.

In an alternate embodiment hereof the cutting blade comprises a cylindrical body, having at least two asymmetrical protrusions on the cylindrical body which cooperate to define a marker for enabling differentiation.

For a more complete understanding of the present invention, reference is made to the following detailed description and accompanying drawing. In the drawing, like reference characters refer to like parts throughout the several views in which:

DESCRIPTION OF THE INVENTION

In accordance with the present invention, there is provided a donor corneal tissue cutting blade provided with integrally formed with a marker or means for marking which enable or facilitate identification of the anterior and posterior sections or portions of the donor corneal tissue to enable proper placement in the anterior cavity of the recipient.

Figure 1:
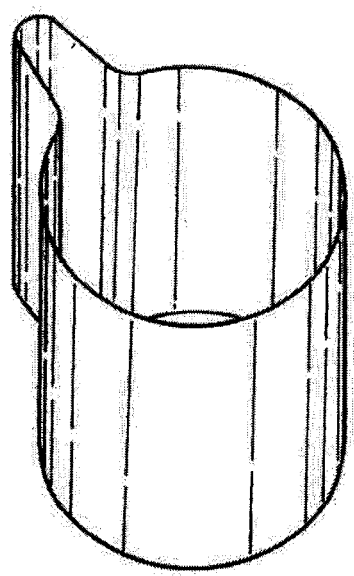
FIG. 1 is a perspective view of a cornea cutting blade known as a "Bala Punch"
Figure 2:
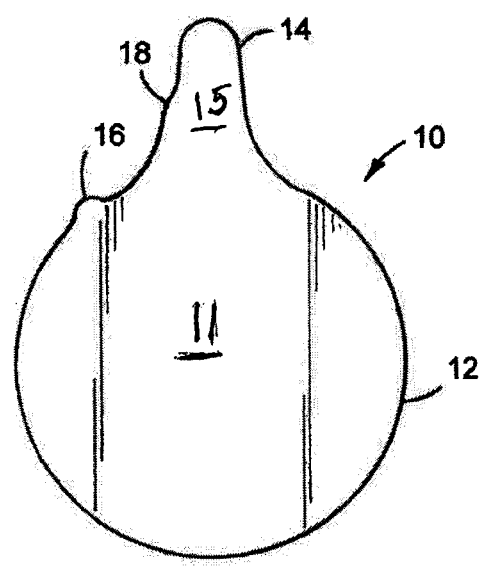
FIG. 2 is a top plan view of a cutting blade in accordance herewith for use in conjunction with a donor corneal punch.

Now, and with reference to the drawing and, FIGS. 1 and 2, there is depicted therein, a first embodiment hereof which is predicated on a Bala Punch corneal donor cutting blade, and, which is, generally, denoted at 10. A "Bala Punch" is a donor corneal cutting blade which has been developed by Dr. Chandrashekar Balachandran and has been disclosed at professional meetings and is presently being readied for commercial availability.

The blade 10 hereof, has a substantially cylindrical body 12 and a U-shaped extension or "tail" 14 integrally formed therewith. The body and tail cooperate to form a keyhole or keyway, as shown.

The body 12 has an open interior 11. The tail or extension 14, likewise, has an open interior 15 in communication with the interior 11 of the body 12.

The blade 10 is provided with indicia comprising a protrusion 16. The protrusion 16 defines a marker or means for marking to denote, as desired, the anterior or posterior side of the donor corneal tissue. Preferably, the protrusion may be provided on either side of the body and projects outwardly therefrom.

Optionally, a protrusion 18 may be provided on the tail 14 and project outwardly therefrom. Where present the protrusion 18 defines a maker in the same manner as protrusion 16 and, thus, cooperates therewith.

The protrusions 16, 18 of the blade 10 are asymmetric and are integrally formed with the blade 10. The asymmetry enables the tissue orientation to be readily identified by using the irregularities in the resulting shape of the tail and/or body.

By providing the asymmetric configuration to the blade prior to implanting the tissue for the transplant, the surgeon can identify the positioning of the blade to readily identify the correct anterior and posterior positioning of the tissue in the anterior cavity of the eye.

It should be noted that the tail 14, in and of itself, does provide means for identifying the position or orientation. However, the optional protrusion 18 on the tail provides a further reference point or marker that is more readily visible than the protrusions on the main body of the blade inside the tissue carrier that is used to inject or implant the tissue into the patient's eye.

Figure 3:
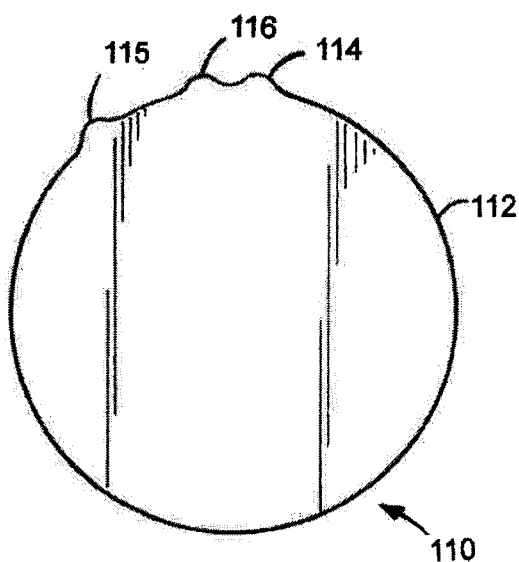
FIG. 3 is a plan view of an alternate embodiment of the cutting blade hereof.

Now, and with reference to FIG. 3, in an alternate embodiment hereof, there is depicted a circular cutting blade 110. The blade 110 is a substantially cylindrical body 112 having an open interior 111. The blade 110 has at least one and, preferably, a plurality of protrusions 114 formed on the cylindrical body 112. Where more than one protrusion is employed, the protrusions, as with the first embodiment, are asymmetric and define means for marking the anterior and posterior sides of the donor tissue.

These protrusion(s) 114 is/are used in the same manner as with the first embodiment to enable the surgeon to readily identify the anterior and posterior positions of the donor tissue and, similarly, are integral with the blade 112.

Thus, it is to be appreciated that by providing these irregularities there is no impairment of the actual condition of donor tissue. Rather the asymmetry assists the surgeon in identifying the anterior and posterior portions of the donor tissue for implantation into the patient's eye.

Manufacturing of the cutting blade, whether one with the "tail" or a conventional cylindrical cutting blade with the asymmetric conformation, generally, comprises grinding a cylindrical surgical stainless-steel blank to proper thickness, grinding a cutting edge, and, then, annealing the blade.

Annealing generally takes place in a heated vacuum chamber held at about 1×10-3 Torr at a temperature ranging from about 1525° F. to about 1575° F. and, preferably, from 1550° F. for about 30 to about 75 minutes. Thereafter, the blank is vacuum cooled at a rate of about 55° F. per hour until the blank is cooled to a temperature of below about 940° F. Next, the blank/blade is cooled at any convenient rate while maintaining the vacuum until it reaches the ambient.

Figure 4:
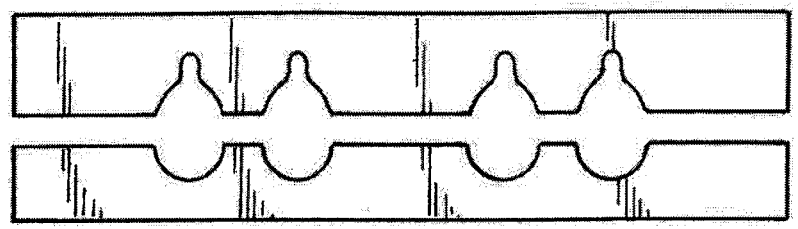
FIG. 4 is a top view of a fixture used in forming the cutting blade of FIG. 1.

Thereafter, the so-ground, annealed blade is then placed within a two-piece fixture such as that shown in FIG. 4 at 210 and stamped using either manual, hydraulic or pneumatic pressure. The blade is, thus, conformed to the shape of the die and which includes the tail and/or body protrusions.

After the configuration is achieved, the blade is case hardened by placing it under vacuum in a suitable heated vacuum chamber at a pressure of about 1×10-3 Torr or better and at a temperature of about 1900° F. to about 1950° F. for about sixty to about ninety minutes.

Thereafter, the case-hardened blade is frozen for about at least one hundred and twenty minutes at a temperature of about −120° F. in an inert atmosphere such as a nitrogen or argon. Next, the blade is tempered in air in a suitable oven for at least about an additional one hundred and twenty minutes at a temperature ranging from about 300° F. to about 350° F. Lastly, the blade is removed from the oven and air cooled until it reaches the ambient and is ready for use.

Alternatively, the cutting blade may be fabricated by deploying a single female shape such as that shown at 212 in FIG. 4.

A matching male part is, then, used to form the tail and body projection(s).

Further, during the heat tracking stage, an external plug of the appropriate diameter for the body is used during the hardening stage.

Figure 5:
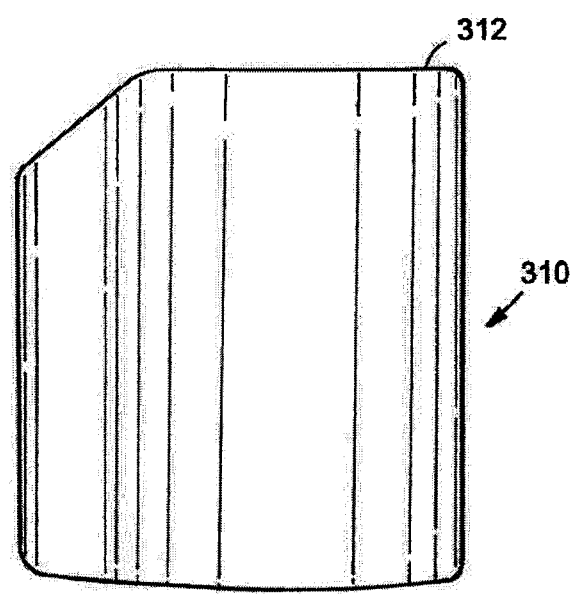
FIG. 5 is a side view of a cutting blade fabricated by an alternate method of manufacture.

It is also contemplated, and as shown in FIG. 5, the blade 310 has its cutting edge 312 ground at varying heights relative to the bottom end of the blade prior to annealing. In this manner, after forming and heat treating, the edge 312 matches the spherical well in the punch block.

It should be noted that in practicing the present invention, it is not to be limited to the formation of the protrusions. Although not shown in the drawing, the irregularity or asymmetric markers may comprise an indentation or indentations, as well as a combination of a protrusion(s) and indentation(s), etc. The important factor is to be able to differentiate between the anterior and posterior sections in the patient and which side should be the anterior and which should be the posterior when placing the anterior section of the cornea transplant in the patient's eye within the anterior chamber.

It is to be appreciated from the preceding that there has been described herein a cutting blade which eliminates the need for the Gentian violet ink.

Having thus described the invention, what is claimed is:

1. A corneal cutting blade for harvesting donor corneal tissue, comprising:
    (a) a substantially cylindrical body having a cylindrical wall and an open interior to receive harvested donor corneal tissue; and
    (b) means for marking the corneal tissue formed on the wall and integral therewith to enable differentiation between the anterior and posterior sides of the corneal tissue, the means for marking comprising:
    a U-shaped extension integrally formed with the body wall and extending laterally outwardly therefrom, along the length of the cylindrical wall.

2. The cutting blade of claim 1, wherein the means for marking further comprises at least one protrusion cooperable with the extension and provided on the body wall and extending laterally outwardly therefrom.

3. The cutting blade of claim 2, which further includes a protrusion formed on the extension, the protrusion being asymmetric with the protrusion formed on the body wall and cooperating therewith to further define the means for marking.

4. The cutting blade of claim 1, wherein the means for marking further comprises a protrusion integrally formed on the extension and laterally projecting outwardly therefrom.

* * * * *